United States Patent [19]

Smith

[11] Patent Number: 4,838,684
[45] Date of Patent: Jun. 13, 1989

[54] APPARATUS FOR AND METHOD OF TESTING VISUAL ACUITY

[76] Inventor: Jeffery W. Smith, 9151 Sutton Ct., Orland Park, Ill. 60462

[21] Appl. No.: 12,506

[22] Filed: Feb. 9, 1987

[51] Int. Cl.⁴ .............................................. A61B 3/00
[52] U.S. Cl. ..................................... 351/239; 351/209
[58] Field of Search ........ 351/209, 210, 223, 239–245, 351/246; 350/246; 128/745, 76.5

[56] References Cited

U.S. PATENT DOCUMENTS 1,415,511  5/1922  Bausch ................................ 350/246
1,827,954  10/1931  Ohm .................................... 351/243
3,623,799  11/1971  Millodot .............................. 351/239

Primary Examiner—Rodney B. Bovernick
Assistant Examiner—Jay Ryan
Attorney, Agent, or Firm—Mann, McWilliams, Zummer and Sweeney

[57] ABSTRACT

A hand-held, rotatable, cylindrical drum provided with a series of sequentially interchangeable stimulus patterns that cover the drum which, when rotated in front of a patient, induces optokinetic nystagmus which is used to non-verbally assess the visual acuity of a patient.

3 Claims, 1 Drawing Sheet

U.S. Patent    Jun. 13, 1989    4,838,684
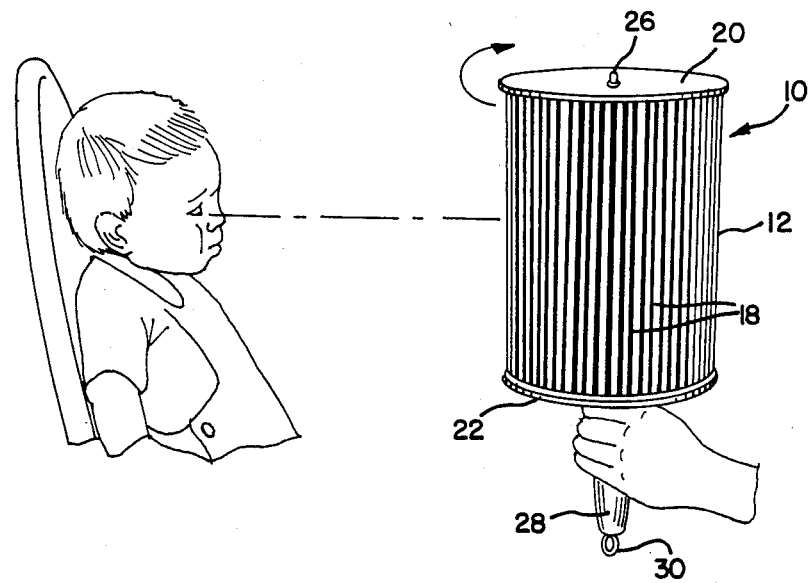
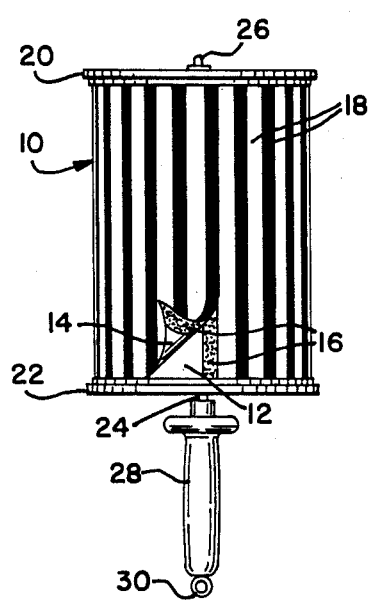
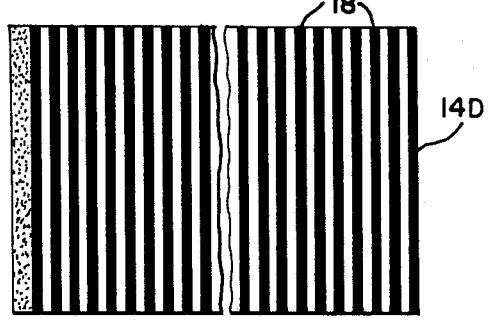
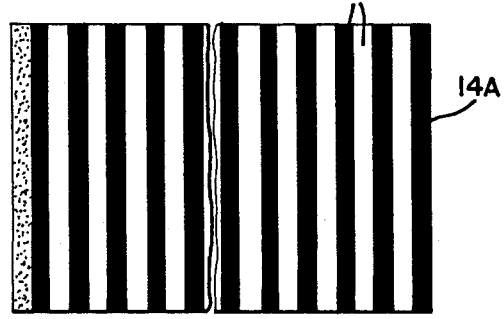

APPARATUS FOR AND METHOD OF TESTING VISUAL ACUITY

BACKGROUND OF THE INVENTION

The present invention is directed to a device for non-verbal assessment of visual acuity. Numerous arrangements of this general type are shown in the prior art U.S. Pat. Nos. 2,033,529, 2,352,500, 2,385,992, 2,463,813, 3,355,237, 3,477,779, and 3,623,799.

One method of assessing visual acuity, known as Ohm's method, includes a number of separate drums, the surfaces of which consist of alternating black and white stripes of varying widths or dots, figures or similar configurations. Ohm used different drums with different patterns for each testing level. This meant that several drums were necessary.

SUMMARY OF THE INVENTION

The present invention provides a hand-held portable drum for non-verbal assessment of visual acuity including a series of stimulus covers adapted to be individually, releasably secured around the drum. Each stimulus cover is provided with a grating pattern of alternating, adjacent, vertically disposed bars of equal width of two different colors. Each cover of the series has bars narrower in width than the bars of the preceding cover. The clinician assesses visual acuity by monitoring the optokinetic nystagmus response induced by the subject viewing the rotating drum as the covers in the series are replaced beginning with the cover having the widest bars.

BRIEF DESCRIPTION OF THE DRAWINGS

FIG. 1 is a perspective view of the rotating device with a stimulus cover in place being viewed by a subject.

FIG. 2 is a side view of the apparatus at rest showing a stimulus cover partially secured in place around the device.

FIG. 3 is a side view of one of the series of stimulus covers with a smaller grating pattern.

FIG. 4 is a side view of one of the series of stimulus covers with a larger grating pattern.

DETAILED DESCRIPTION OF THE INVENTION

As shown in FIGS. 1 and 2, a hand-held, portable, visual acuity testing device is provided. The device includes a drum 10, a series of removable stimulus covers, 14A-14F, a spindle 24, and a handle 28. The drum 10 is substantially cylindrical and has a side wall 12. A series of six rectangular stimulus covers 14A-14F are provided, the covers 14 being sized to fit around the drum 10. The covers 14 are provided with a Velcro ® closure 16 for releasably securing them around the drum 10. Any of a number of other releasable securement mechanisms may be used in place of the closure 16 illustrated in FIG. 2. This permits the covers 14 to be easily and quickly removed or attached.

The covers 14 are provided on their faces with a grating pattern consisting of alternately adjacent, vertically disposed bars 18 of two different alternating colors, for example, black and white, and of equal width. Other colors may be used to test for color blindness. Each cover in the series has bars of a width narrower than the bars of the cover which preceded it in the series. The width of the bars of the stimulus covers vary from ⅜" for cover 14A to ⅜" for cover 14B, ¼" for cover 14C, 3/16" for cover 14D, ⅛" for cover 14E, and 3/32" for cover 14F. Under most circumstances, a series of six covers will be sufficient for testing. FIGS. 3 and 4 show covers with bars of varying widths, FIG. 3 showing cover 14D, with FIG. 4 illustrating 14A.

A substantially circular first flange 20, provided with a groove around the circumference of the underside, is disposed atop the drum 10, the top of the side wall 12 fitting into the groove. When the flange 20 is in place, it extends radially beyond the periphery of the drum 10 thereby limiting the vertical movement of the stimulus cover 14. A second flange 22, substantially identical to the first flange 20, is disposed on the bottom of the drum 10 in the same manner.

The drum 10 and corresponding flanges 20 and 22 are rotatably mounted about the spindle 24 which extends just above the top of the flange 20. A nut 26 secures the drum 10 in place while allowing rotation of the drum about the spindle. A handle 28 is provided at the end of the spindle 24 below the second flange 22. A loop 30 is provided at the end of the handle 28, so the device may be easily hung for storage.

When it is desired to non-verbally assess a subject's visual acuity, the stimulus cover with the largest grating pattern 14A is placed around the drum 10. The drum is then held in front of the subject at a distance of approximately 16" and rotated at a speed of about 30 rpm. The clinician then observes the subject's eyes as the subject watches the rotating drum and cover. The observation of a regular pendular movement of the subject's eyes, an optokinetic nystagmus response, by the clinician indicates that the subject can resolve the grating pattern. Optokinetic nystagmus is an involuntary physiological reflex caused by symmetric objects moving in a constant direction in the patient's field of vision. The clinician then removes the cover 14A and replaces it with the next cover in the series, 14B, with the next smaller grating pattern. The clinician follows this procedure until he observes no optokinetic nystagmus response from the subject. This indicates that the point has been reached when the subject can no longer visually resolve the grating pattern at which time the regular pendular eye movement stops. The last cover to induce an optokinetic nystagmus response indicates the subject's threshold of visual acuity. This size of grating pattern can be translated into standard Snellen measurement, namely, 20/20, 20/60, 20/200.

It is possible to test both monocular and binocular visual acuity employing this method. Occluding one eye is done for monocular testing. By orientating the drum in different viewing planes, the different oculomotor muscles can be evaluated for paresis or paralysis. If covers having stripes colored other than black and white are used, testing for the detection of color blindness rather than visual acuity can be performed.

Thus it has been shown that the present invention provides a hand-held, portable visual acuity testing device which permits use of a simple method of non-verbal assessment of visual acuity, color blindness and ocular paresis and paralysis employing interchangeable stimulus covers. A simple three to five minute screening offers direct measurement of visual acuity for early routing assessment of the visual system and for monitoring of treatment of the visual system. The apparatus and method can be used to evaluate the visual acuity of children at an age prior to their ability to verbally communicate.

Various features of the invention have been particularly shown and described in connection with the illustrated embodiment of the invention, however, it must be understood that these particular arrangements merely illustrate and that the invention is to be given its fullest interpretation within the terms of the appended claims.

What is claimed is:

1. A hand-held, portable visual acuity testing device including a spindle having a handle at one end, a cylindrical drum rotatably mounted on said spindle, said drum including a first flange disposed on top of said drum extending beyond the periphery of said drum and a second flange disposed on the bottom of said drum also extending beyond the periphery of said drum, said first and second flanges defining a locating surface therebetween and a series of removable stimulus covers each of which is adapted to be releasably secured around said drum and consists of alternately adjacent, vertically disposed bars of equal width of two different colors, each cover in said series having bars of narrower width than the cover which precedes it in said series, whereby said drum may be used to measure the visual acuity of a patient.

2. A hand-held, portable visual acuity testing device as in claim 1 wherein said bars are alternately colored black and white.

3. A hand-held, portable visual acuity testing device as in claim 1 in which the width of the vertical bars of said stimulus covers in said series varies from ½" to 3/32".

* * * * *